United States Patent [19]
Bundy

[11] Patent Number: 5,932,728
[45] Date of Patent: Aug. 3, 1999

[54] PHARMACEUTICALLY ACTIVE TRICYCLIC AMINES

[75] Inventor: Gordon L. Bundy, Kalamazoo, Mich.

[73] Assignee: Pharmacia & Upjohn Company, Kalamazoo, Mich.

[21] Appl. No.: 08/994,901

[22] Filed: Dec. 19, 1997

Related U.S. Application Data

[60] Provisional application No. 60/035,223, Jan. 8, 1997, and provisional application No. 60/043,749, Apr. 9, 1997.

[51] Int. Cl.$^6$ .................................................. C07D 487/04
[52] U.S. Cl. .......................... 544/250; 544/115; 514/267; 514/232.8
[58] Field of Search ..................................... 544/250, 115; 514/267

[56] References Cited

U.S. PATENT DOCUMENTS 5,502,187  3/1996  Ayer et al. ............................... 544/117
5,795,986  8/1998  Bundy et al. ............................ 544/115

FOREIGN PATENT DOCUMENTS 9320078  10/1993  WIPO .
9626941   9/1996  WIPO .

OTHER PUBLICATIONS

Eger et al. *J. Heterocyclic. Chem.,* 24, p. 425 (1987).

*Primary Examiner*—Emily Bernhardt
*Attorney, Agent, or Firm*—Bruce Stein

[57] ABSTRACT

Pyrimido[4,5-b]indoles (IV)

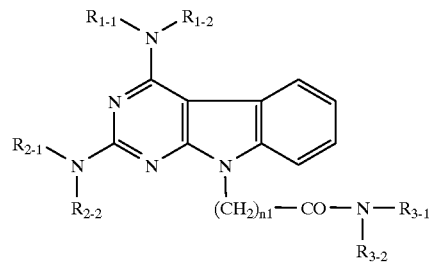

and pyrimido[4,5-b]indole salts (V) useful in treating asthma are disclosed as well as process for their preparation.

7 Claims, No Drawings

PHARMACEUTICALLY ACTIVE TRICYCLIC AMINES

CROSS REFERENCE TO RELATED APPLICATIONS

This application claims the benefit of U.S. provisional application Ser. Nos. 60/035,223 filed Jan. 8, 1997 and 60/043,749 filed Apr. 9, 1997, under 35 USC §119(e)(i).

BACKGROUND OF THE INVENTION

1. Field of the Invention

The pharmaceutically active pyrimido[4,5-b]indoles (IV) of the present invention are useful as pharmaceuticals to treat a number of diseases and injuries.

2. Description of the Related Art

International publication WO92/02500-A discloses 2-phenylindole derivatives useful for treating asthma, allergic disorders, thrombosis and ischaemia.

The *J. Heterocyclic. Chem.*, 24, 425 (1987) discloses pyrrolopyrimidines where the amino groups on the pyrimidine moiety are free and unsubstituted, whereas the compounds of the present invention are substituted aminopyrrolopyrimidines.

International Publication WO91/04254 discloses pyrrolo[2,3-d]pyrimidines where the groups substituted on the pyrrolo ring are simple. In two of the positions the groups are —H, halogen or alkyl. In the third it is —H, alkyl or aralkyl.

International Publication WO93/20078 based on PCT/US93/02188 and International Publication WO96/26941 based on PCT/US96/02397 disclose various pyrimido[4,5-b]indoles which have pharmaceutical utility. The present invention is a selection invention from International Publication WO93/20078 and WO96/26941.

SUMMARY OF INVENTION

Disclosed are pyrimido[4,5-b]indoles of the formula (IV)

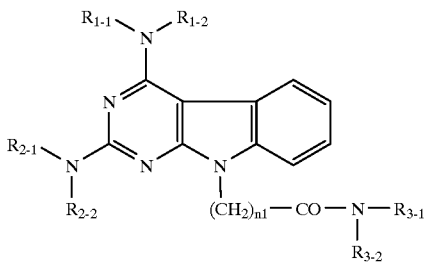

(IV)

where $R_{1-1}$ and $R_{1-2}$ are taken together with the attached nitrogen atom to form a heterocyclic ring selected from the group consisting of 1-pyrrolidinyl, 1-piperidinyl and 4-morpholinyl;

where $R_{2-1}$ and $R_{2-2}$ are taken together with the attached nitrogen atom to form a heterocyclic ring selected from the group consisting of 1-pyrrolidinyl, 1-piperidinyl and 4-morpholinyl with the proviso that the heterocyclic ring of $R_{1-1}/R_{1-2}$ is the same as that of $R_{2-1}/R_{2-2}$;

where $n_1$ is 1 thru 3;

where $R_{3-1}$ is:
(1) —H,
(2) $C_1$–$C_3$ alkyl,
(3) -φ;

where $R_{3-2}$ is:
(1) —H,
(2) —CH$_2$-[2-pyridinyl],
(3) —CH$_2$-[3-pyridinyl],
(4) —CH$_2$-[4-pyridinyl],
(5) —CH$_2$-[CH(OH)]$_4$—CH$_2$—OH,
(7) —CH$_2$—COOH,
(8) —OH,
(9) —CH$_2$—CH$_2$—CH$_2$—CH$_2$—OH,
(10) —CH$_2$—CH$_2$—CH$_2$—CO—OH, and where $R_{3-1}$ and $R_{3-2}$ are taken together with the attached nitrogen atom to form a heterocyclic ring selected from the group consisting of:
(1) 1-pyrrolidinyl,
(2) 1-piperidinyl,
(3) 4-morpholinyl,
(4) 2-hydroxy-1-pyrrolidinyl,
(5) 3-hydroxy-1-pyrrolidinyl,
(6) 1-prolinyl and pharmaceutically acceptable salts thereof.

Also disclosed is (2,4-di-1-pyrrolidinyl-9H-pyrimido[4,5-b]indol-9-yl)acetic acid, t-butyl ester.

Further disclosed is (2,4-di-1-pyrrolidinyl-9H-pyrimido[4,5-b]indol-9-yl)acetic acid and pharmaceutically acceptable salts thereof.

DETAILED DESCRIPTION OF THE INVENTION

The pyrimido[4,5-b]indoles (IV) and the pharmaceutically acceptable salts thereof (V) of the present invention are produced by methods known to those skilled in the art from known starting compounds. The invention is the pyrimido[4,5-b]indoles (IV) and the pharmaceutically acceptable salts thereof (V), not the chemistry used to produce them.

The pyrimido[4,5-b]indoles (IV) of the present invention can be prepared by the processes set forth in International Publications WO93/20078 and WO92/26941 and the processes of CHARTS A–C. There are two preferred methods to produce the pyrimido[4,5-b]indoles (IV) of the present invention. The first method uses the chemistry set forth in CHARTS A and B. The second method uses the chemistry set forth in CHARTS A and C. Both processes use the two steps set forth in CHART A.

In CHART A, the starting alcohols (I) are known to those skilled in the art or can be readily prepared from known compounds by methods known to those skilled in the art. See for example, *J. Med. Chem.*, 38, 4161–3 (1995). The alcohol (I) is converted to a leaving group derivative (II) by methods well known to those skilled in the art. Suitable leaving groups, -$X_1$, include mesylate, tosylate and para —SO$_2$—φ—NO$_2$. It is preferred that $X_1$ is mesylate. The alcohol with a leaving group (II) is then converted to the corresponding secondary amine (III) by treatment with sodium cyanide and a trace of a hindered non-nucleophilic tertiary amine (in solvents such as DMF, DMSO or acetonitrile). The secondary amine (III) is the branching point for the two processes. In the first process, CHART B, the secondary amine (III) is alkylated with a molecular fragment which contains the alkyl side chain and the amide, —(CH$_2$)$_{n1}$—CO—N(R$_{3-1}$)(R$_{3-2}$) where $n_1$ is one thru three thereby directly producing the desired pyrimido[4,5-b]indole (IV). It is preferred that $n_1$ is one. The pyrimido[4,5-b]indole (IV) is an amine base and as such forms pyrimido[4,5-b]indole salts (V) in the usual manner, see EXAMPLEs 2–6.

Alternatively, when $n_1$ is 1, the secondary amine (III) is alkylated with t-butyl bromoacetate to form the butyl is 1 ester (VI). The butyl ester (VI) is then hydrolyzed by known means to the corresponding acid (VII). The acid (VII) is then converted by known means to the corresponding pyrimido [4,5-b]indole amides (IV) and/or pyrimido[4,5-b]indole salt (V).

It is preferred that the pyrimido[4,5-b]indoles (IV) be in the form of a pharmaceutically acceptable salt, pyrimido[4,5-b]indole salt (V), and it is preferred that the salt be selected from the group consisting of hydrochloride, hydrobromide, maleate and methanesulfonate.

The pyrimido[4,5-b]indoles (IV) are useful in treating/preventing asthma (and reduction of mucous formation/secretion in the lung); dermatitis, of the atopic, inflammatory, allergic or contact form (and the reduction of itching, weeping oozing and thickening of the skin, which accompanies the dermatitis condition); rhinitis, of the atopic, inflammatory or seasonal allergic form (and the reduction of itching, weeping, oozing and mucus secretion of the nasal mucosa, which accompanies the rhinitis condition); conjunctivitis, blepharitis, iritis or combinations thereof, of the atopic, allergic, seasonal or inflammatory form (and the reduction of itching, weeping, oozing and mucus secretion of the eye or its parts, which accompanies the conjunctivitis, blepharitis, iritis or combinations thereof condition).

The pyrimido[4,5-b]indoles (IV) are useful in treating/preventing asthma (and reduction of mucous formation/secretion in the lung). In treating excess mucous secretion and asthma, the pyrimido[4,5-b]indoles (IV) are administered orally, IV and by inhalation in the standard dose. In treating excess mucous secretions the oral dose of the pyrimido[4,5-b]indoles (IV) used is from about 0.05 to about 20 mg/kg/day. The frequency of administration is one thru 4 times daily. The oral administration of the pyrimido [4,5-b]indoles (IV) to treat excess mucous secretions may go on for months or even years. The susceptible individuals can be pre-treated a few hours before an expected problem. The IV dose is about 0.05 to about 20 mg/kg/day. The aerosol formulation contains about 0.01 to about 1.0% of the tricyclic amides (IV) and is administered or used about four times daily as needed. The pyrimido[4,5-b]indoles (IV) are also useful in treating/preventing dermatitis, of the atopic, inflammatory, allergic or contact form (and the reduction of itching, weeping oozing and thickening of the skin, which accompanies the dermatitis condition). In treating dermatitis and the associated signs and symptoms, pyrimido[4,5-b]indoles (IV) are administered orally, and IV in the standard dose, and in a topical application of varying topical formulations (solution, suspension, cream, ointment, lotion, powder, gel or other recognized admixture) of pyrimido[4,5-b]indoles (IV) used is from about 0.01% to about 20% concentration of pyrimido[4,5-b]indoles (IV) to the base materials. The frequency of administration is one thru 4 times daily. The oral and topical administration of the pyrimido[4,5-b]indoles (IV) to treat the signs and/or symptoms of dermatitis may go on for months or even years. The susceptible individuals can be pre-treated a few hours before an expected problem. The IV dose is about 0.05 to about 20 mg/kg/day.

The pyrimido[4,5-b]indoles (IV) are useful in treating/preventing rhinitis, of the atopic, inflammatory or seasonal allergic form (and the reduction of itching, weeping, oozing and mucus secretion of the nasal mucosa, which accompanies the rhinitis condition). In treating rhinitis and the associated signs and symptoms, pyrimido[4,5-b]indoles (IV) are administered orally, and IV in the standard dose, and in a topical application of varying topical formulations (solution, suspension, cream, ointment, lotion, powder, gel or other recognized admixture) of pyrimido[4,5-b]indoles (IV) used is from about 0.01% to about 20% concentration of pyrimido[4,5-b]indoles (IV) to the base materials. The frequency of administration is one thru 4 times daily. The oral and topical administration of the pyrimido[4,5-b] indoles (IV) to treat the signs and/or symptoms of rhinitis may go on for months or even years. The susceptible individuals can be pre-treated a few hours before an expected problem. The IV dose is about 0.05 to about 20 mg/kg/day.

The pyrimido[4,5-b]indoles (IV) are useful in treating/preventing conjunctivitis, blepharitis, iritis or combinations thereof, of the atopic, allergic, seasonal or inflammatory form (and the reduction of itching, weeping, oozing and mucus secretion of the eye or its parts, which accompanies the conjunctivitis, blepharitis, iritis or combinations thereof condition). In treating conjunctivitis, blepharitis, iritis or combinations thereof and the associated signs and symptoms, pyrimido[4,5-b]indoles (I) are administered orally, and IV in the standard dose, and in a topical application of varying topical formulations (solution, suspension, cream, ointment, lotion, powder, gels or other recognized admixture) of pyrimido[4,5-b]indoles (IV) used is from about 0.001% to about 20% concentration of pyrimido[4,5-b]indoles (IV) to the base materials. The frequency of administration is one thru 4 times daily. The oral and topical administration of the pyrimido[4,5-b]indoles (IV) to treat the signs and/or symptoms of conjunctivitis, blepharitis, iritis or combinations thereof may go on for months or even years. The susceptible individuals can be pre-treated a few hours before an expected problem. The IV dose is about 0.05 to about 20 mg/kg/day.

The term treatment or treating as used in this patent is used broadly and includes both treatment of an existing condition as well as preventing the same condition from occurring where such is possible as is well known to those skilled in the art. For example, the pyrimido[4,5-b]indoles (IV) can be used to treat existing asthma conditions and to prevent future ones from occurring; existing dermatitis conditions and to prevent future ones from occurring; existing rhinitis conditions and to prevent future ones from occurring; existing conjunctivitis, blepharitis, iritis or combinations thereof conditions and to prevent future ones from occurring.

The exact dosage and frequency of administration depends on the particular pyrimido[4,5-b]indoles (IV) used, the particular type of condition being treated, the severity of the condition being treated, the age, weight, general physical condition of the particular patient, other medication the individual may be taking as is well known to those skilled in the art and can be more accurately determined by measuring the blood level or concentration of the tricyclic amides (IV) in the patient's blood and/or the patient's response to the particular condition being treated.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention $(C_1$–$C_3)$alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and $(C_1$–$C_3)$ alkoxy$(C_1$–$C_3)$alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. DEFINITIONS

All temperatures are in degrees Centigrade.

TLC refers to thin-layer chromatography.

THF refers to tetrahydrofuran.

DMF refers to dimethylformamide.

DMSO refers to dimethylsulfoxide.

Saline refers to an aqueous saturated sodium chloride mixture.

IR refers to infrared spectroscopy.

NMR refers to nuclear (proton) magnetic resonance spectroscopy, chemical shifts are reported in ppm ($\delta$) downfield from tetramethylsilane.

TMS refers to tetramethylsilane.

-$\phi$ refers to phenyl ($C_6H_5$).

MS refers to mass spectrometry expressed as m/z or mass/charge unit. [M+H]$^+$ refers to the positive ion of a parent plus a hydrogen atom. EI refers to electron impact. CI refers to chemical ionization. FAB refers to fast atom bombardment.

HRMS refers to high resolution mass spectrometry.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pharmaceutically acceptable salts include the salts of the following acids hydrochloric, hydrobromic, sulfuric, phosphoric, nitric, citric, methanesulfonic $CH_3$—$(CH_2)_{n1}$—COOH where $n_1$ is 0 thru 4, HOOC—$(CH_2)_{n1}$—COOH where n is as defined above, HOOC—CH=CH—COOH, $\phi$—COOH.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

9-[2-(Methanesulfonyloxy)ethyl]-2,4-di-1-pyrrolidinyl-9H-pyrimido[4,5-b]indole (II)

9-[2-(Hydroxy)ethyl]-2,4-di-1-pyrrolidinyl-9H-pyrimido [4,5-b]indole (I, *J. Med. Chem.*, 38, 4161–3 (1995) is reacted with methanesulfonyl chloride by means known to those skilled in the art to give the title compound.

Example 2

1-[(2,4-Di-1-pyrrolidinyl-9H-pyrimido[4,5-b]indol-9-yl)acetyl]pyrrolidine monohydrochloride also known as (2,4-di-1-pyrrolidinyl-9H-pyrimido[4,5-b] indol-9-yl)acetic acid, pyrrolidine amide, monohydrochloride (IV/V)

A stirred mixture of 9-[2-(methanesulfonyloxy)ethyl]-2, 4-di-1-pyrrolidinyl-9H-pyrimido[4,5-b]indole (II, EXAMPLE 1 and WO/9626941-A1, 165 g), sodium cyanide (180 g), water (360 mL) and DMSO (3000 mL) are heated at 100° for 18 hr. It is important that the starting mesylate contain traces of triethylamine either left over from its preparation, or added intentionally. The mixture is cooled to 20–25°, diluted with water (approximately 6,000 mL) and filtered. The solid is washed with water to remove excess cyanide, then triturated with acetone. Filtration and drying gives 2,4-di-1-pyrrolidinyl-9H-pyrimido[4,5-b]indole (III), mp 209–211°; NMR (CDCl$_3$) 7.88, 7.22, 7.09, 3.95, 3.67 and 1.98 $\delta$; MS (m/z, FAB, M+H) 308.

A mixture of 2,4-di-1-pyrrolidinyl-9H-pyrimido[4,5-b] indole (III, 93.1 g) in THF (2150 mL) is cooled to –40° and treated over 30 min with n-butyllithium/hexane (1.6 M, 246 mL). After 30 min longer at –40°, a mixture of bromoacetylpyrrolidine [*J. Med. Chem.*, 30, 20–24 (1987), 93.1 g] in THF (750 mL) is added over 15 min. The reaction mixture is allowed to warm to 20–25° 2 hr and is then re-cooled to –40° and filtered. The solids are partitioned between methylene chloride and water and the organic layer is dried and concentrated to give the free base of the title compound (IV), mp=201–204°; NMR (CDCl$_3$) 7.87, 7.38, 7.21–7.08, 5.05, 3.92, 3.62, 3.48, 3.33, 1.96 and 1.85 $\delta$.

Treatment of a mixture the above free base (IV, 94.5 g) in methanol with one equivalent of methanolic hydrochloric acid gives the title compound (V), mp=250–255°; MS (m/z, M+ observed)=418.2476, calculated for $C_{24}H_{30}N_6O$= 418.2481. (The salt component, hydrochloride in this case, does not show up in the MS which is normal).

Example 3

(2,4-Di-1-pyrrolidinyl-9H-pyrimido[4,5-b]indol-9-yl)acetic acid, pyrrolidine amide, sulfate (V)

Following the general procedure of the last paragraph of EXAMPLE 2 and making non-critical variations but starting with (2,4-di-1-pyrrolidinyl-9H-pyrimido[4,5-b]indol-9-yl) acetic acid, pyrrolidine amide (IV, EXAMPLE 2) and using sulfuric acid, the title compound is obtained, mp=175–180°.

Example 4

(2,4-Di-1-pyrrolidinyl-9H-pyrimido[4,5-b]indol-9-yl)acetic acid, pyrrolidine amide, methanesulfonate salt (V)

Following the general procedure of the last paragraph of EXAMPLE 2 and making non-critical variations but starting with (2,4-di-1-pyrrolidinyl-9H-pyrimido[4,5-b]indol-9-yl)acetic acid, pyrrolidine amide (IV, EXAMPLE 2) and using methanesulfonic acid, the title compound is obtained, mp=199–200°.

Example 5

(2,4-Di-1-pyrrolidinyl-9H-pyrimido[4,5-b]indol-9-yl)acetic acid, pyrrolidine amide, maleate salt (V)

Following the general procedure of the last paragraph of EXAMPLE 2 and making non-critical variations but starting with (2,4-di-1-pyrrolidinyl-9H-pyrimido[4,5-b]indol-9-yl)acetic acid, pyrrolidine amide (IV, EXAMPLE 2) and using maleic acid, the title compound is obtained, mp=150–151°.

Example 6

(2,4-Di-1-pyrrolidinyl-9H-pyrimido[4,5-b]indol-9-yl)acetic acid, pyrrolidine amide, phosphate salt (V)

Following the general procedure of the last paragraph of EXAMPLE 2 and making non-critical variations but starting with (2,4-di-1-pyrrolidinyl-9H-pyrimido[4,5-b]indol-9-yl)acetic acid, pyrrolidine amide (IV, EXAMPLE 2) and using phosphoric acid, the title compound is obtained, mp=200–201°.

Example 7

(2,4-Di-1-pyrrolidinyl-9H-pyrimido[4,5-b]indol-9-yl)acetic acid, t-butyl ester (VI)

n-Butyllithium (4.26 mL; 1.6 M in hexane) is added to a mixture of 2,4-di-1-pyrrolidinyl-9H-pyrimido[4,5-b]indole (III, EXAMPLE 2, 2.0 g) in THF (50 mL) at −15°. After 1 hr, t-butyl bromoacetate (1.27 g) in THF (20 mL) is added, and the mixture is stirred for 2 hr at 20–25°. The mixture is partitioned between aqueous sodium bicarbonate and methylene chloride, and the organic layer is dried and concentrated. Chromatography of the crude product (silica gel; hexane/methylene chloride/ethyl acetate (70/25/5) gives the title compound, mp=131–133°; NMR (CDCl$_3$) 7.87, 7.15, 4.92, 3.92, 3.61, 1.96 and 1.43 δ; MS (m/z=421 (M$^+$).

Example 8

(2,4-Di-1-pyrrolidinyl-9H-pyrimido[4,5-b]indol-9-yl)acetic acid, hydrochloride (VII)

A mixture of (2,4-Di-1-pyrrolidinyl-9H-pyrimido[4,5-b]indol-9-yl)acetic acid, t-butyl ester (VI, EXAMPLE 7, 2.5 g) in aqueous hydrochloric acid (1.0 M) is heated at reflux for 2 hr. The mixture is then cooled and concentrated to approximately one third of the original volume. Filtration of the resulting solid gives the title compound, mp 250–253°; NMR (CDCl$_3$) 8.07, 7.35, 5.21, 4.10, 3.73 and 2.11 δ; IR (neat) 2925, 1736, 1627, 1608, 1568, 1445 and 1193 cm$^{-1}$.

Example 9

(2,4-Di-1-pyrrolidinyl-9H-pyrimido[4,5-b]indol-9-yl)acetic acid, morpholine amide (IV) and monohydrochloride (V)

A mixture of (2,4-di-1-pyrrolidinyl-9H-pyrimido[4,5-b]indol-9-yl)acetic acid, hydrochloride (VII, EXAMPLE 8, 1.41 g) in methylene chloride (20 mL) and acetonitrile (20 mL) is treated with triethylamine (1.08 mL), cooled to −5°, then treated with isobutyl chloroformate (0.50 mL). The mixture is stirred for 20 min, then treated with morpholine (0.83 mL). The mixture is stirred for 2 hr, then partitioned between methylene chloride and aqueous sodium bicarbonate. The layers are separated and the organic layer is dried and concentrated, and the residue is purified by chromatography (silica gel; acetone/methylene chloride, 10/90), to give the free base of the title compound, mp 220–222°.

A mixture of the free base (IV) of the title compound (1.3 g) in methanol (50 mL) is treated with one equivalent of methanolic hydrochloric acid. Recrystallization of the resulting solid from methanol/ethyl acetate gives the title compound, mp=238–240°; NMR (CH$_3$OD) 8.0, 7.42, 7.35, 7.27, 5.31, 3.98, 3.80, 3.69, 3.59 and 2.06 δ.

Example 10

(2,4-Di-1-pyrrolidinyl-9H-pyrimido[4,5-b]indol-9-yl)acetic acid, 2-aminomethylpyridine amide (IV) and dihydrochloride (V)

Following the general procedure of EXAMPLE 9 and making non-critical variations but using 2-(aminomethyl)pyridine in place of morpholine and two equivalents of hydrochloric acid in the salt formation, the free base (IV) of the title compound is obtained which is converted to the title compound, mp=162–165°; NMR (CH$_3$OD) 8.77, 8.58, 8.00, 7.47, 7.37, 7.30, 5.33, 4.81, 4.10, 3.74 and 2.12 δ.

Example 11

(2,4-Di-1-pyrrolidinyl-9H-pyrimido[4,5-b]indol-9-yl)acetic acid, amide (IV) and hydrochloride (V)

Following the general procedure of EXAMPLE 9 and making non-critical variations but using ammonia in place of morpholine, the free base (IV) of the title compound is obtained which is converted to the title compound, mp=260–264°; NMR (CH$_3$OD) 8.06, 7.36, 5.12, 4.05, 3.67 and 2.08 δ.

Example 12

(2,4-Di-1-pyrrolidinyl-9H-pyrimido[4,5-b]indol-9-yl)acetic acid, 1-amino-1-deoxysorbitol amide (IV) and hydrochloride (V)

Following the general procedure of EXAMPLE 9 and making non-critical variations but using 1-amino-1-deoxysorbitol in place of morpholine, the free base (IV) of the title compound is obtained which is converted to the title compound, mp=122–126°; MS (m/z) calculated=529.2774, observed 529.2779.

Example 13

(2,4-Di-1-pyrrolidinyl-9H-pyrimido[4,5-b]indol-9-yl)acetic acid, proline amide (IV) and hydrochloride (V)

Following the general procedure of EXAMPLE 9 and making non-critical variations but using proline in place of morpholine, the free base (IV) of the title compound is obtained which is converted to the title compound, mp=118–120°; MS (m/z) calculated=462.2379, observed=462.2371.

Example 14

(2,4-Di-1-pyrrolidinyl-9H-pyrimido[4,5-b]indol-9-yl)acetic acid, glycine amide (IV) and hydrochloride (V)

Following the general procedure of EXAMPLE 9 and making non-critical variations but using glycine in place of morpholine, the free base (IV) of the title compound is obtained which is converted to the title compound, mp=155–160°; NMR (CH₃OD) 8.04, 7.47, 7.37, 7.29, 5.17, 4.00, 3.66, 3.30 and 2.08 δ.

Example 15

(2,4-Di-1-pyrrolidinyl-9H-pyrimido[4,5-b]indol-9-yl)acetic acid, hydroxylamine amide (IV) and hydrochloride (V)

Following the general procedure of EXAMPLE 9 and making non-critical variations but using O-benzylhydroxylamine in place of morpholine, the free base (IV) of the title compound is obtained which is converted to O-benzyl derivative of the title compound, mp=184–186°. This material (523 mg) is debenzylated by hydrogenation in the presence of palladium on carbon (10%, 504 mg), DMF (50 mL) hydrogen (45 psi for 5.5 hr). Filtration and concentration of the filtrate gives the free base (IV) of the title compound, mp=147–150°. Formation of the hydrochloride salt is performed according to EXAMPLE 9 to give the title compound, mp=210–212°; MS (m\z) calcuated 381.2039, observed 381.2028.

Example 16

(2,4-Di-1-pyrrolidinyl-9H-pyrimido[4,5-b]indol-9-yl)acetic acid, 3-hydroxypyrrolidine amide (IV) and salt (V)

Following the general procedure of EXAMPLE 9 and making non-critical variations but using 3-hydroxypyrrolidine in place of morpholine, the title compound is obtained, mp=224–226°; MS (m\z)=434.1 ($M^+$) as well as the hydrochloride salt, mp=145–150°.

Example 17

(2,4-Di-1-pyrrolidinyl-9H-pyrimido[4,5-b]indol-9-yl)acetic acid, 4-amino-1-butanol amide (IV) and hydrochloride (V)

Following the general procedure of EXAMPLE 9 and making non-critical variations but using 4-amino-1-butanol in place of morpholine, the free base (IV) of the title compound is obtained, mp=199–201° which is converted to the salt of the title compound, mp=108–110°; MS (m\z)= calculated=436.2587, observed=436.2574.

Example 18

(2,4-Di-1-pyrrolidinyl-9H-pyrimido[4,5-b]indol-9-yl)acetic acid, 4-aminobutyric acid amide (IV)

Following the general procedure of EXAMPLE 9 and making non-critical variations but using 4-aminobutyric acid in place of morpholine, the title compound is obtained, mp=215–220°; MS (m\z) calculated=450.2379, observed 450.2379.

Example 19

(2,4-Di-1-pyrrolidinyl-9H-pyrimido[4,5-b]indol-9-yl)acetic acid, 2-hydroxypyrrolidine amide (IV)

Following the general procedure of EXAMPLE 9 and making non-critical variations but using 4-aminobutyraldehyde diethyl acetal in place of morpholine, the acetal intermediate is obtained, mp=153–156°. The acetal is hydrolyzed following the general procedure of *J. Org. Chem.*, 48, 3667 (1983). A mixture of the acetal intermediate (103 mg), sodium iodide (80 mg), and methyltrichlorosilane (0.05 mL) in acetonitrile (2 mL) is stirred at 20–25° for 30 min. The reaction mixture is then partitioned between aqueous sodium bicarbonate, sodium thiosulfate and methylene chloride, the layers separated and the organic layer is dried and concentrated. Chromatography of the residue (silica gel; acetone/methylene chloride, 10/90) gives the title compound (free base), mp=185–190°; MS (m\e)=calculated=434.2430; observed=434.2421. NMR (CDCl₃) 7.87, 7.65, 7.26, 7.16, 5.47, 5.28, 4.88, 4.84, 4.79, 3.93, 3.66–3.61 and 1.99–1.91 δ.

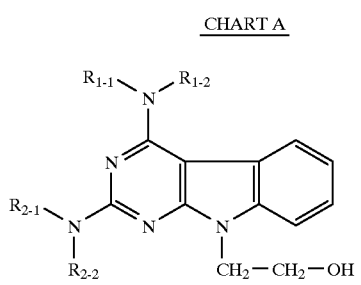

-continued

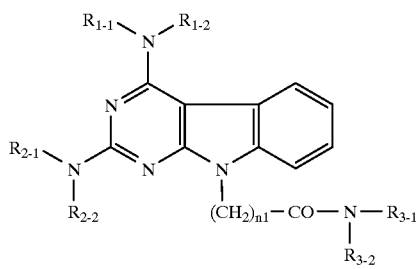
(IV)

Salt of (IV)

CHART C

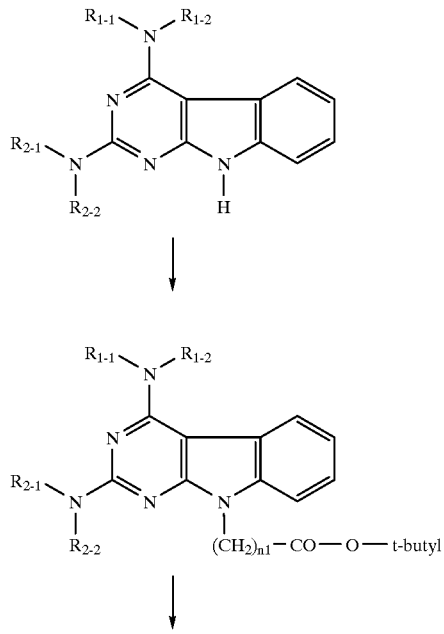
(III)

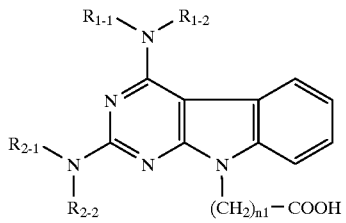
(VI)

(VII)

-continued

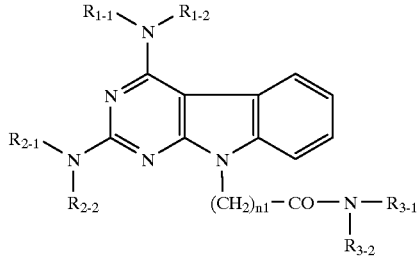
(IV)

I claim:
1. Pyrimido[4,5-b]indoles of the formula (IV)

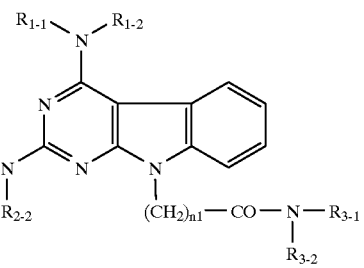
(IV)

where $R_{1-2}$ and $R_{1-2}$ are taken together with the attached nitrogen atom to form 1-pyrrolidinyl;
where $R_{2-1}$ and $R_{2-2}$ are taken together with the attached nitrogen atom to form 1-pyrrolidiny;
where $n_1$ is 1 thru 3;
where $R_{3-1}$ is:
 (1) —H,
where $R_{3-2}$ is:
 (1) —H,
 (2) —CH$_2$—[2-pyridinyl],
 (3) —CH$_2$—[3-pyridinyl],
 (4) —CH$_2$—[4-pyridinyl],
 (5) —CH$_2$—[CH(OH)]$_4$—CH$_2$—OH,
 (8) —OH,
and where $R_{3-1}$ and $R_{3-2}$ are taken together with the attached nitrogen atom to form a heterocyclic ring selected from the group consisting of:
 (1) 1-pyrrolidinyl,
 (2) 1-piperidinyl,
 (3) 4-morpholinyl,
 (4) 2-hydroxy-1-pyrrolidinyl,
 (5) 3-hydroxy-1-pyrrolidinyl,
 (6) 1-prolinyl and pharmaceutically acceptable salts thereof.
2. Tricyclic amines of formula (IV) according to claim 1 where $n_1$ is 1.
3. Tricyclic amines of formula (IV) according to claim 1 where $R_{3-1}$ and $R_{3-2}$ are taken together with the attached nitrogen atoms to form 1-pyrrolidinyl.
4. Tricyclic amines of formula (IV) according to claim 1 where the pharmaceutically acceptable salts are selected from the group consisting of hydrochloride, sulfate, methanesulfonate, maleate and phosphate.

5. Tricyclic amines of formula (IV) according to claim 1 which are selected from the group consisting of:

(2,4-di-1-pyrrolidinyl-9H-pyrimido[4,5-b]indol-9-yl) acetic acid, pyrrolidine amide, (2,4-di-1-pyrrolidinyl-9H-pyrimido[4,5-b]indol-9-yl) acetic acid, morpholine amide, (2,4-di-1-pyrrolidinyl-9H-pyrimido[4,5-b]indol-9-yl) acetic acid, 2-aminomethylpyridine amide, (2,4-di-1-pyrrolidinyl-9H-pyrimido[4,5-b]indol-9-yl) acetic acid, amide, (2,4-di-1-pyrrolidinyl-9H-pyrimido[4,5-b]indol-9-yl) acetic acid, 1-amino-1-deoxysorbitol amide (2,4-di-1-pyrrolidinyl-9H-pyrimido[4,5-b]indol-9-yl) acetic acid, proline amide, (2,4-di-1-pyrrolidinyl-9H-pyrimido[4,5-b]indol-9-yl) acetic acid, glycine amide, (2,4-di-1-pyrrolidinyl-9H-pyrimido[4,5-b]indol-9-yl) acetic acid, hydroxylamine amide, (2,4-di-1-pyrrolidinyl-9H-pyrimido[4,5-b]indol-9-yl) acetic acid, 3-hydroxypyrrolidine amide, (2,4-di-1-pyrrolidinyl-9H-pyrimido[4,5-b]indol-9-yl) acetic acid, 4-amino-1-butanol amide, (2,4-di-1-pyrrolidinyl-9H-pyrimido[4,5-b]indol-9-yl) acetic acid, 4-aminobutyric acid amide, (2,4-di-1-pyrrolidinyl-9H-pyrimido[4,5-b]indol-9-yl) acetic acid, 2-hydroxypyrrolidine amide.

6. Tricyclic amines of formula (IV) according to claim 5 which is (2,4-di-1-pyrrolidinyl-9H-pyrimido[4,5-b]indol-9-yl) acetic acid, pyrrolidine amide.

7. Tricyclic amines of formula (IV) according to claim 5 which is (2,4-di-1-pyrrolidinyl-9H-pyrimido[4,5-b]indol-9-yl) acetic acid, pyrrolidine amide, monohydrochloride, (2,4-di-1-pyrrolidinyl-9H-pyrimido[4,5-b]inol-9-yl) acetic acid, pyrrolidine amide, sulfate, (2,4-di-1-pyrrolidinyl-9H-pyrimido[4,5-b]indol-9-yl) acetic acid, pyrrolidine amide, methanesulfonate salt, (2,4-di-1-pyrrolidinyl-9H-pyrimido[4,5-b]indol-9-yl) acetic acid, pyrrolidine amide, maleate salt and (2,4-di-1-pyrrolidinyl-9H-pyrimido[4,5-b]indol-9-yl) acetic acid, pyrrolidine amide, phosphate salt.

* * * * *